United States Patent
Meyer et al.

(10) Patent No.: US 10,117,683 B2
(45) Date of Patent: Nov. 6, 2018

(54) SPINAL ROD LOCKING HOLDER

(71) Applicant: K2M, Inc., Leesburg, VA (US)

(72) Inventors: Robert Meyer, Leesburg, VA (US);
Kevin R. Strauss, Columbia, MD (US);
Larry McClintock, Gore, VA (US)

(73) Assignee: K2M, Inc., Leesburg, VA (US)

( * ) Notice: Subject to any disclaimer, the term of this patent is extended or adjusted under 35 U.S.C. 154(b) by 219 days.

(21) Appl. No.: 15/183,019

(22) Filed: Jun. 15, 2016

(65) Prior Publication Data

US 2016/0287295 A1    Oct. 6, 2016

Related U.S. Application Data

(62) Division of application No. 13/923,666, filed on Jun. 21, 2013, now Pat. No. 9,393,054.

(60) Provisional application No. 61/664,211, filed on Jun. 26, 2012.

(51) Int. Cl.
*A61B 17/70* (2006.01)

(52) U.S. Cl.
CPC ...... *A61B 17/7079* (2013.01); *A61B 17/7074* (2013.01); *A61B 17/7083* (2013.01)

(58) Field of Classification Search
CPC . A61B 17/88; A61B 17/7074; A61B 17/7079; A61B 17/7083; A61B 17/7082; A61B 17/7085; A61B 17/7086; A61B 17/7088; A61B 17/7089; A61B 17/7091; B25B 13/463

See application file for complete search history.

(56) References Cited

U.S. PATENT DOCUMENTS

| | | | |
|---|---|---|---|
| 1,450,641 A | 4/1923 | Ograbisz | |
| 4,276,791 A | 7/1981 | Thompson | |
| 4,576,167 A | 3/1986 | Noiles | |
| 4,993,288 A | 2/1991 | Anderson et al. | |
| 5,224,403 A | 7/1993 | Rueb | |
| 5,582,080 A | 12/1996 | Barmore | |
| 6,263,765 B1 | 7/2001 | McCamley | |
| 7,249,539 B2 | 7/2007 | Decaprio | |
| 8,366,714 B2 * | 2/2013 | Jones | A61B 17/7083 606/104 |
| 8,661,945 B1 | 3/2014 | ElDessouky | |
| 9,393,054 B2 | 7/2016 | Meyer et al. | |
| 9,610,107 B2 * | 4/2017 | Lindner | A61B 17/7086 |
| 9,788,869 B2 * | 10/2017 | Stad | A61B 17/7083 |
| 9,907,596 B2 * | 3/2018 | McClintock | A61B 17/8863 |

(Continued)

*Primary Examiner* — Jacqueline Johanas
*Assistant Examiner* — Tessa Matthews
(74) *Attorney, Agent, or Firm* — Carter, DeLuca, Farrell & Schmidt, LLP

(57) ABSTRACT

A spinal rod locking holder includes an outer body, a handle assembly at a proximal end of the outer body, a locking assembly within a distal portion of the outer body, and a sprocket assembly at the distal end of the outer body. The handle assembly includes a moveable handle operatively associated with the sprocket assembly to selectively engage and release an end of a spinal rod. The locking assembly including a bearing operatively associated with a pawl such that when the moveable handle is compressed the bearing extends the pawl into contact with an outer surface of the sprocket assembly. The sprocket assembly including sprocket sections configured to compress against the end of the spinal rod when the pawl engages the outer surface of the sprocket assembly.

17 Claims, 5 Drawing Sheets

(56) References Cited

U.S. PATENT DOCUMENTS

| | | |
|---|---|---|
| 2007/0107559 A1 | 5/2007 | Bryson et al. |
| 2008/0077136 A1* | 3/2008 | Triplett .............. A61B 17/7004 606/86 A |
| 2009/0105774 A1* | 4/2009 | Jones ................ A61B 17/7083 606/86 A |
| 2010/0094359 A1 | 4/2010 | Techiera et al. |
| 2010/0222828 A1 | 9/2010 | Stad et al. |
| 2011/0218581 A1 | 9/2011 | Justis |
| 2015/0018892 A1* | 1/2015 | Lindner ............. A61B 17/7083 606/86 A |
| 2015/0073485 A1* | 3/2015 | Butler ................ A61B 17/7083 606/279 |

\* cited by examiner

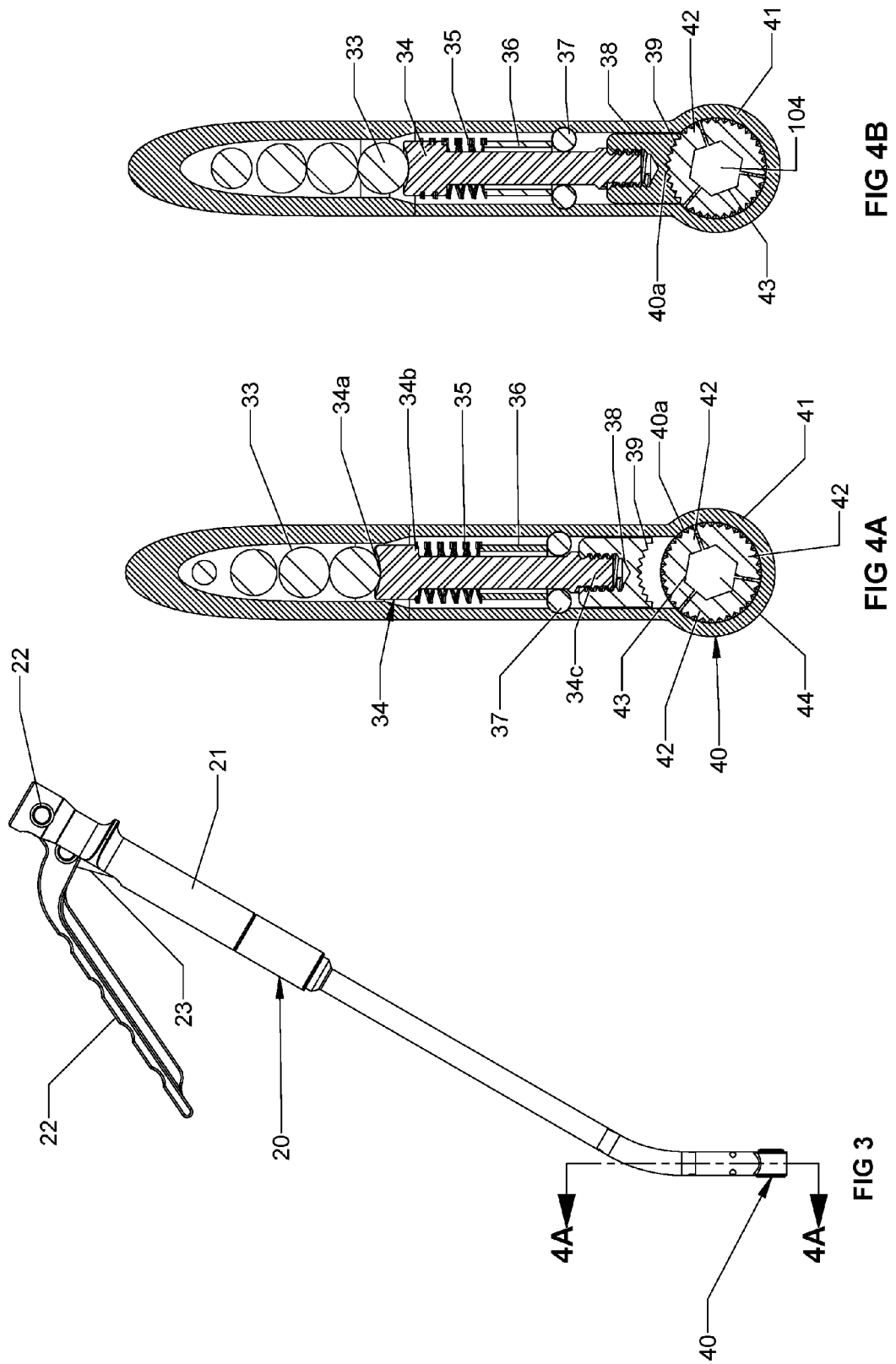

SPINAL ROD LOCKING HOLDER

CROSS-REFERENCE TO OTHER APPLICATIONS

This application is a divisional of U.S. patent application Ser. No. 13/923,666, filed Jun. 21, 2013, which claims priority to and the benefit of U.S. Provisional Patent Application Ser. No. 61/664,211, filed Jun. 26, 2012. The entire contents of each of these applications are incorporated by reference herein.

BACKGROUND

1. Technical Field

The present disclosure relates to a system and method for operating on the spine. More particularly, the present disclosure relates to a locking holder for manipulating a spinal rod.

2. Discussion of Related Art

The spinal column is a complex system of bones and connective tissues that provide support for the human body and protection for the spinal cord and nerves. The adult spine is comprised of an upper and lower portion. The upper portion contains 24 discrete bones, which are subdivided into three areas including 7 cervical vertebrae, 12 thoracic vertebrae and 5 lumbar vertebrae. The lower portion is comprised of the sacral and coccygeal bones. The cylindrical shaped bones, called vertebral bodies, progressively increase in size from the upper portion downwards to the lower portion.

An intervertebral disc along with two posterior facet joints cushion and dampen the various translational and rotational forces exerted upon the spinal column. The intervertebral disc is a spacer located between two vertebral bodies. The facets provide stability to the posterior portion of adjacent vertebrae. The spinal cord is housed in the canal of the vertebral bodies. It is protected posteriorly by the lamina. The lamina is a curved surface with three main protrusions. Two transverse processes extend laterally from the lamina, while the spinous process extends caudally and posteriorly. The vertebral bodies and lamina are connected by a bone bridge called the pedicle.

The spine is a flexible structure capable of a large range of motion. There are various disorders, diseases, and types of injury which restrict the range of motion of the spine or interfere with important elements of the nervous system. The problems include, but are not limited to scoliosis, kyphosis, excessive lordosis, spondylolisthesis, slipped or ruptured discs, degenerative disc disease, vertebral body fracture, and tumors. Persons suffering from any of the above conditions typically experience extreme or debilitating pain and often times diminished nerve function. These conditions and their treatments can be further complicated if the patient is suffering from osteoporosis, or bone tissue thinning and loss of bone density.

Spinal fixation apparatuses are widely employed in surgical processes for correcting spinal injuries and diseases. When the disc has degenerated to the point of requiring removal, there are a variety of interbody implants that are utilized to take the place of the disc. These include polyetheretherketone ("PEEK") interbody spacers, metal cages, and cadaver and human bone implants. In order to facilitate stabilizing the spine and keeping the interbody in position, other implants are commonly employed, including longitudinally linked rods secured to coupling elements, which in turn are secured to the bone by spinal bone fixation fasteners such as pedicle screws, hooks, and others. The opposing pair of longitudinally linked rods is commonly disposed along the long axis of the spine via a posterior approach. Pedicle screws are utilized to capture these rods and can be manufactured from any biocompatible material, including cobalt chrome, stainless steel, titanium, and PEEK. It is desired to perform these procedures in a minimally invasive manner to minimize pain and reduce recovery time for the patient. Therefore, a need exists for a minimally invasive rod reducer, compressor, distractor system that can deliver the rod into the head of the pedicle screw or bone anchor while maintaining the proper screw and rod construct alignment.

SUMMARY

In an aspect of the present disclosure, a spinal rod locking holder includes an outer body, a handle assembly, a locking assembly, and a sprocket assembly. The outer body includes an inner channel extending along the longitudinal axis. The handle assembly is positioned at a proximal end of the outer body and includes a moveable handle and a fixed handle. The locking assembly is positioned within the inner channel and includes a pawl. The sprocket assembly is positioned at a distal end of the outer body and includes a plurality of sprocket sections. The plurality of sprocket sections form a cylinder having a hexagonal opening and an outer surface. The pawl is configured to engage the outer surface of the sprocket sections to radially fix the sprocket sections relative to the outer body.

The moveable handle can have a non-compressed position such that the pawl is retracted away from the outer surface of the plurality of sprocket sections. When the pawl is retracted away from the outer surface, the plurality of sprocket sections are rotatable with the outer body. The movable handle can have a compressed position such that the pawl engages the outer surface of the plurality of sprocket sections. When the pawl is engaged with the outer surface, the plurality of sprocket sections are radially fixed within the outer body.

In embodiments, the outer body includes a bend between proximal and distal portions of the outer body defining an angle. The angle between the proximal and distal portions of the outer body can be in the range of about 90° to about 180°.

In some embodiments, the wrench includes an inner shaft positioned within the inner chamber between and operatively associating the handle assembly and the locking assembly. The inner shaft being slidable proximally and distally along the longitudinal axis. The locking assembly can include a bearing positioned between a distal end of the inner shaft and the pawl. In some embodiments, the bearing is a plurality of bearings configured to cooperate with the bend in the outer body. In embodiments, the distal end of the pawl includes teeth configured to engage a set of teeth on the outer surface of the plurality of sprocket sections. In some embodiments, the sprocket assembly includes a sprocket biasing member configured to urge the plurality of sprocket sections radially outward.

The handle assembly can include a camming link and a handle shaft. The camming link is coupled to the moveable handle and the handle shaft. When the moveable handle is compressed towards the fixed handle, the camming link moves the handle shaft distally. In embodiments, the moveable handle is biased towards the non-compressed position by a handle biasing member positioned about the handle shaft.

According to another aspect of the present disclosure, a method includes positioning a portion of a spinal rod, sliding a locking holder over a spinal rod, compressing a moveable handle, rotating the locking holder, and releasing the moveable handle. Positioning the spinal rod may include positioning a portion of the spinal rod within a head of a bone anchor. Sliding a locking holder over a spinal rod includes sliding a sprocket assembly of a locking holder over an end of the spinal rod. The sprocket assembly intimately contacts the end of the spinal rod. Compressing a moveable handle includes operatively associating the moveable handle with the sprocket assembly to lock the end of the spinal rod within the sprocket assembly and to radially fix the sprocket assembly relative to an outer body of the locking holder when the moveable handle is compressed at an initial radial position. Rotating the locking holder includes rotating the locking holder about the longitudinal axis of the spinal rod to rotate the spinal rod towards a desired radial orientation while maintaining the moveable handle in the compressed position. Releasing the movable handle includes releasing the movable handle when the spinal rod is in the desired radial orientation.

Rotating the locking holder may further include reaching a rotational limit, releasing the moveable handle, returning the locking holder to the initial radial position, recompressing the moveable handle, rotating the locking holder to further rotate the rod towards a desired orientation. Reaching, releasing, returning, recompressing, and rotating may be repeated until the spinal rod is in the desired radial orientation.

The method may further include attaching a rod reducing device to the head of a bone anchor before releasing the moveable handle. The method may also include utilizing the rod reducing device to push the spinal rod into the head of the bone anchor after the spinal rod is in the desired radial orientation and before releasing the moveable handle. The method may also include locking the spinal rod to the head of the bone screw before releasing the moveable handle.

Further, to the extent consistent, any of the aspects described herein may be used in conjunction with any or all of the other aspects described herein.

BRIEF DESCRIPTION OF THE DRAWINGS

Various aspects of the present disclosure are described hereinbelow with reference to the drawings, wherein:

FIG. 3 is a side view of the wrench of FIG. 1;

FIG. 4A is a cross-sectional view taken along the line 4A-4A of FIG. 3 with the wrench in the open condition;

FIG. 4B is a cross-sectional view of the distal end of the wrench of FIG. 3 with the wrench in the clamped condition;

DETAILED DESCRIPTION

Figure 1:
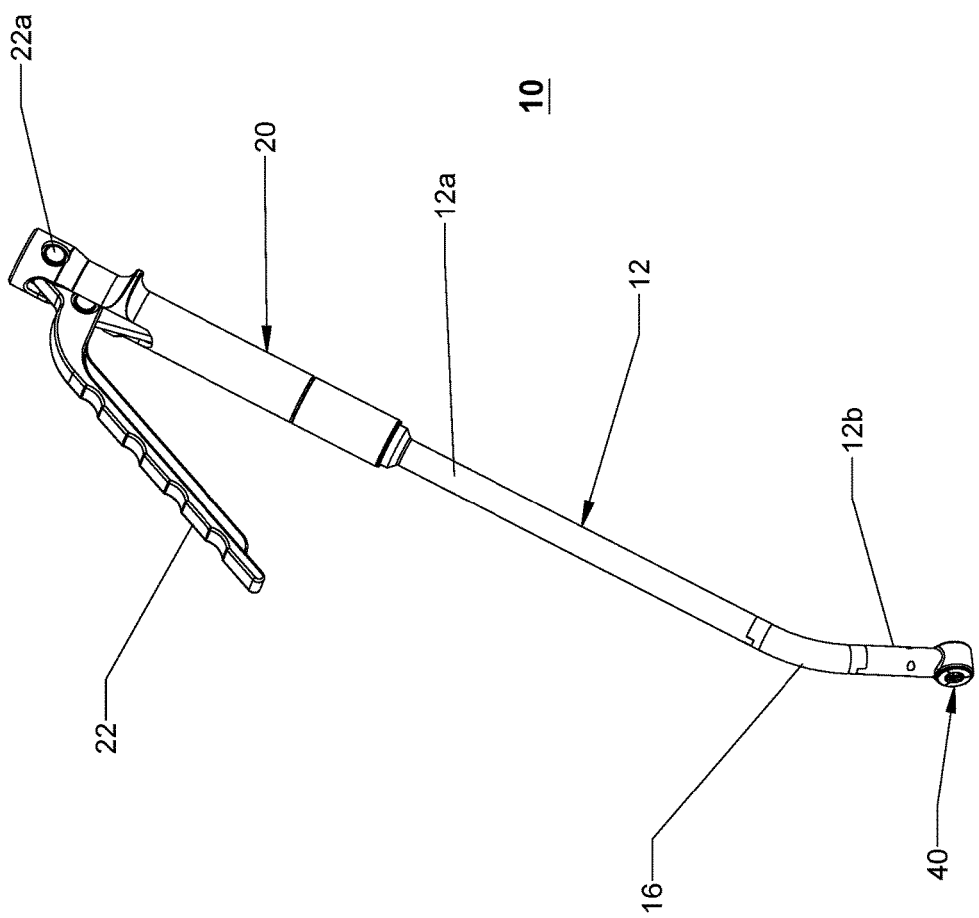
FIG. 1 is a perspective view of the a locking holder in accordance with the present disclosure.

Embodiments of the present disclosure are now described in detail with reference to the drawings in which like reference numerals designate identical or corresponding elements in each of the several views. As used herein, the term "clinician" refers to a doctor, a nurse, a surgeon, or any other care provider and may include support personnel. Throughout this description, the term "proximal" will refer to the portion of the device or component thereof that is closest to the clinician and the term "distal" will refer to the portion of the device or component thereof that is furthest from the clinician.

Figure 2:
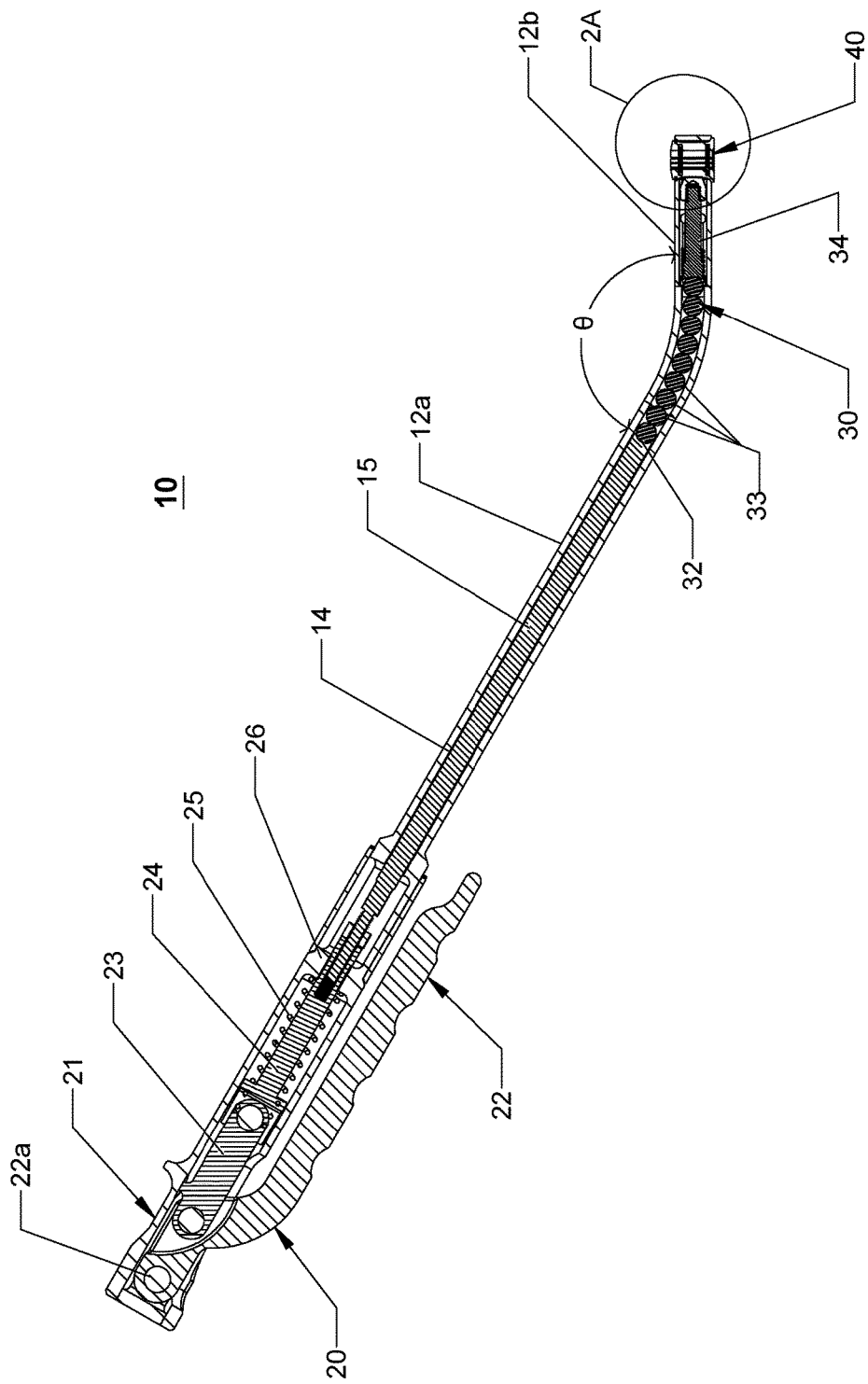
FIG. 2 is a cross-sectional view of the wrench of FIG. 1 taken along the longitudinal axis of the wrench.

Referring now to FIGS. 1 and 2, a spinal rod locking holder 10 in accordance with the present disclosure incorporating an outer body 12, a handle assembly 20, locking assembly 30, and a sprocket assembly 40. Outer body 12 is an elongated tubular member defining an inner channel 14. Outer body 12 can include a bend 16 which defines an angle $\theta$ between a proximal portion 12a and a distal portion 12b of outer body 12 as shown in FIG. 2. Angle $\theta$ is in the range of about 90° to about 180°.

Referring to FIG. 2, handle assembly 20 includes a fixed handle 21, a moveable handle 22, and a proximal shaft 24. Fixed handle 21 is coupled to proximal portion 12a of outer body 12. A proximal portion of moveable handle 22 is disposed within a proximal portion of fixed handle 21. The moveable handle 22 is coupled to fixed handle 21 via a pivoting connection about a pin 22a. Fixed handle 21 can limit the rotation of moveable handle 22 about pin 22a. Moveable handle 22 is also pivotally coupled to a proximal end of a camming link 23. A distal end of camming link 23 is coupled to a proximal end of handle shaft 24. A handle biasing member 25 is disposed about handle shaft 24 engaging a proximal flange 24a of handle shaft 24 and a distal flange 26 of fixed handle 21. A distal end of handle shaft 24 is operatively associated with an inner shaft 15. Inner shaft 15 is positioned within inner channel 14 of outer body 12 operatively associating handle assembly 20 with locking assembly 30.

Moveable handle 22 has a non-compressed position (FIG. 1) and a compressed position (FIG. 2). Moveable handle 22 is biased towards the non-compressed position by handle biasing member 25 urging handle shaft 24 proximally such that camming link 23 engages moveable handle 22 to urge moveable handle 22 towards the non-compressed position. When moveable handle 22 is moved towards the compressed position, towards fixed handle 21, moveable handle 22 moves handle shaft 24 against handle biasing member 25 such that the distal end of handle shaft 24 moves inner shaft 15 distally as described in detail below. Camming link 23 converts the compression of moveable handle 22 to distal and proximal actuation of handle shaft 22.

With reference to FIGS. 2-4B, locking assembly 30 includes bearings 33, a pawl shaft 34, and a pawl 38. A distal end of inner shaft 15 engages bearings 33. In embodiments, the distal end of inner shaft 15 includes a shaft cup 15a configured to mate with the outer surface of a bearing 33. In some embodiments, bearings 33 are positioned within bend 16 between the proximal and distal portions 12a, 12b of outer body 12. In particular embodiments, inner shaft 31 is substantially non-compressible yet flexible to cooperate with bend 16 of outer body 12. The proximal end of pawl shaft 34 engages a bearing 33 and the distal end of pawl shaft 34 is coupled to pawl 38. In embodiments, the proximal end of pawl shaft 34 includes a bearing cup 34a configured to receive a bearing 33. In some embodiments, the distal end of pawl shaft 34 is threadably coupled to pawl 38. A pawl shaft biasing member 35 is positioned about pawl shaft 34 between a protrusion 34b, near the proximal end of pawl shaft 34, and pins 37. Pins 37 are longitudinally fixed within outer body 12 and engage the inner surface of inner channel 14. Pins 37 also engage flats 34c of pawl shaft 34 to prevent pawl shaft 34 from rotating within inner channel 14 and to maintain alignment between pawl shaft 34 and sprocket assembly 40. Pawl shaft biasing member 35 engages flats 34b of pawl shaft 34 to urge pawl shaft 34 proximally. Locking assembly 30 can also include a cylinder 36 positioned about pawl shaft 34 between flats 34b and pins 37. Cylinder 36 is substantially non-compressible and positioned between pawl shaft biasing member 35 and protrusion 34b or snap ring 37. A distal end 39 of pawl 38 is configured to engage an outer surface 40a of sprocket assembly 40 as discussed in detail below. Distal end 39 of pawl 38 and/or outer surface 40a of sprocket assembly 40 can include one of a set of teeth or a high friction surface configured to inhibit rotation of sprocket assembly 40 as discussed in detail below.

Figure 2A:
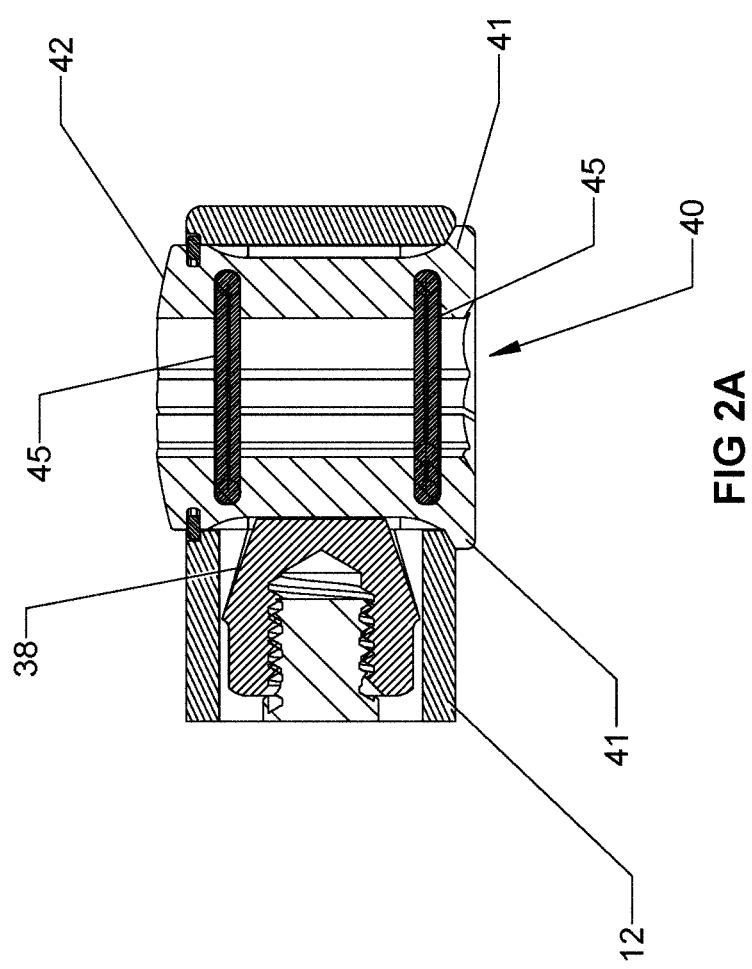
FIG. 2A is an enlargement of the detail area 2A of FIG. 2.

With additional reference to FIG. 2A, sprocket assembly 40 includes sprocket sections 42 and sprocket biasing members 45 positioned within outer wall 41. Outer wall 41 is coupled to the distal end of outer body 12. Sprocket sections 42 are substantially similar and form a cylinder when assembled together within outer wall 41 as shown in FIG. 4A. Inner surface 43 of the cylinder formed by sprocket sections 42 includes flats configured to form a hexagonal opening 44 sized to intimately contact the end 104 of a spinal rod 100 as discussed in detail below. Sprocket biasing members 45 are configured to bias sprocket sections 42 radially towards outer surface 41. Sprocket biasing members 45 can be positioned within radial grooves within inner surface 43. While a hexagonal opening is shown, it is contemplated that the opening formed by sprocket sections 42 can be a star or torx opening, an octagonal opening, a square opening, or any other shape opening complementary to the end of a spinal rod. Moreover, three sprocket sections 42 are shown but it is contemplated that sprocket assembly 40 can include two sprocket sections 42 or that sprocket assembly 40 can include four or more sprocket sections 42.

Referring to FIGS. 4A and 4B, pawl 38 has a retracted position (FIG. 4A) and an extended position (FIG. 4B) and sprocket assembly 40 includes a spaced-apart position (FIG. 4A) and a clamped position (FIG. 4B) corresponding to the retracted position and the extended position of pawl 38 respectively. When pawl 38 is in the retracted position, distal end 39 of pawl 38 is away from or disengaged from outer surface 40a of sprocket assembly 40 and sprocket biasing members 45 urge sprocket sections 42 towards outer surface 41. In the extended and spaced-apart positions moveable handle 22 is in the non-compressed position and an end 104 of a spinal rod 100 is slidable within hexagonal opening 44 and sprocket assembly 40 is free to rotate relative to outer wall 41. As the moveable handle 22 is moved towards the compressed position the pawl moves towards the extended position such that distal end 39 of pawl 38 is engages outer surface 40a of sprocket assembly 40 moving sprocket sections 42 against the sprocket biasing members 45. When inner surface 43 of sprocket sections 42 engage an end 104 of a spinal rod 100, sprocket assembly 40 is in the clamped position such that distal end 104 is secured within sprocket assembly 40 and sprocket assembly 40 is fixed in a radial position relative to outer wall 41 as shown in FIG. 4B.

Figure 5:
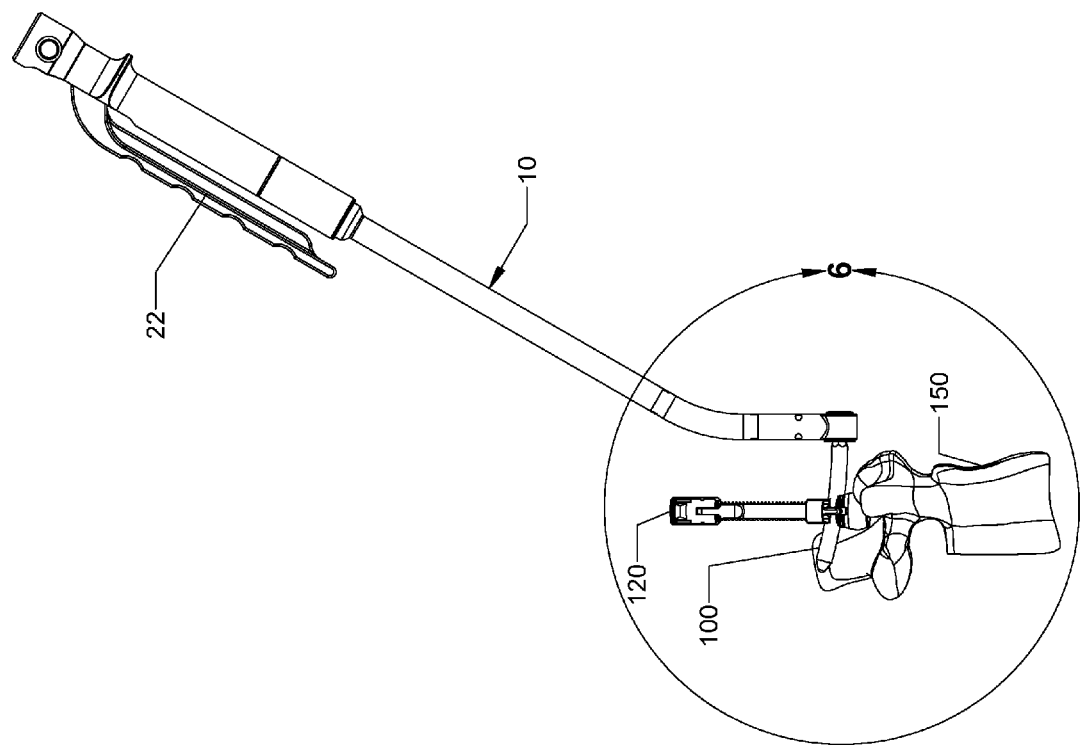
FIG. 5 is a perspective view of the wrench of FIG. 1 positioned during a spinal surgery to engage a spinal rod.
Figure 6:
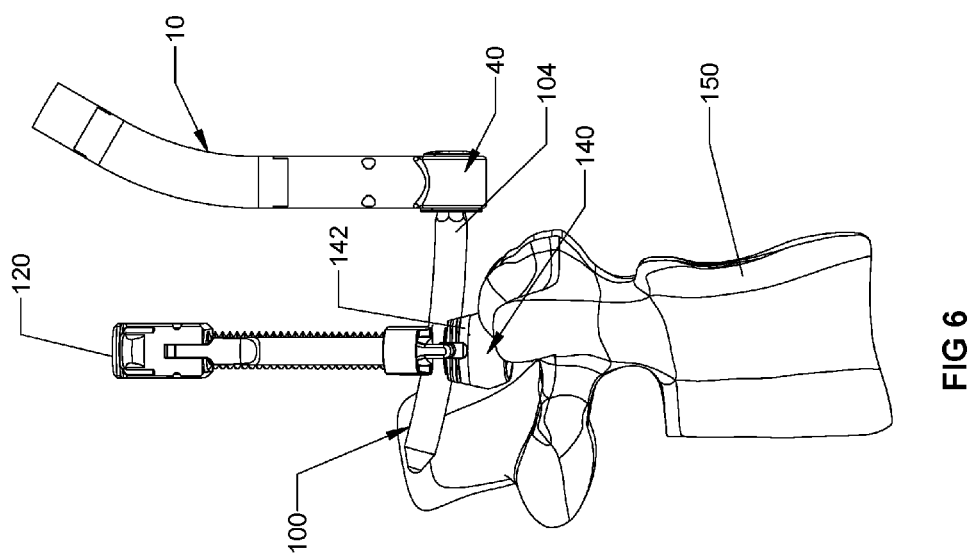
FIG. 6 is an enlargement of the detail area 6 of FIG. 5.

Referring to FIGS. 5 and 6, a method for orientating a spinal rod in accordance with the present disclosure is disclosed. The method includes sliding a sprocket assembly of a locking holder over a spinal rod, compressing a moveable handle of the locking holder to radially fix the sprocket assembly, positioning a portion of a spinal rod, rotating the spinal rod into a desired radial orientation, and releasing the moveable handle to release the end of the spinal rod from the sprocket assembly.

Sliding the sprocket assembly of the locking holder over an end of a spinal rod includes intimately contacting the end of the spinal rod with the sprocket assembly. Sliding the sprocket assembly of the locking holder over an end of a spinal rod may include bending the spinal rod into a desired configuration.

Rotating spinal rod 100 can include applying a radial force to the spinal rod by rotating the handle assembly of locking holder 10 from an initial radial position. Rotating spinal rod 100 may also include reaching a rotational limit of locking holder 10, releasing the moveable handle, rotating the locking holder 10 in a direction away from the desired radial orientation of spinal rod 100, recompressing the moveable handle of locking holder 10, and further rotating spinal rod 100 towards the desired radial orientation. The rotational limit of the locking holder 10 may be set by the interaction of an outer body 12 of locking holder 10 with the spine of the patient. Rotating spinal rod 100 may further include ratcheting locking holder 10 by repeatedly reaching, releasing, rotating, and recompressing until spinal rod 10 is in the desired radial orientation.

The method may include attaching a rod reducing device 120 to the head 142 of the at least one bone anchor 140 before releasing the moveable handle. Such a bone anchor and rod reducing device are disclosed in commonly owned U.S. Patent Pub. No. 2010/0114171 and U.S. Pat. No. 8,308,729, the disclosure of each is hereby incorporated by reference in its entirety. The method may also include utilizing rod reducing device 120 to push spinal rod 100 into the head 142 of the of at least one bone anchor 140 after spinal rod 100 is in the desired radial orientation and before releasing the moveable handle. The method may further include locking the spinal rod 100 to the head 142 of the of at least one bone anchor 140 before releasing the moveable handle. The method may include providing a plurality of bone anchors, implanting the bone anchors, and using the locking holder to position a rod in the plurality of bone anchors, and to rotate the rod positioned in the bone anchors to achieve a desired spinal correction. Alternatively, the rotation of the spinal rod may be performed in order to align the spinal rod with one or more of the bone anchors so that the spinal rod may be approximated to and secured to the bone anchor.

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed:

1. A method for rotating a spinal rod comprising:
   sliding a sprocket assembly of a locking holder over an end of a spinal rod, the sprocket assembly intimately contacting the end of the spinal rod;
   compressing a moveable handle operatively associated with the sprocket assembly to lock the end of the spinal rod within the sprocket assembly and to radially fix the sprocket assembly relative to an outer body of the locking holder;
   positioning a portion of the spinal rod within a head of a bone anchor;

rotating the locking holder from an initial radial position about the longitudinal axis of the spinal rod to rotate the spinal rod towards a desired radial orientation while maintaining the moveable handle in the compressed position; and releasing the moveable handle when the spinal rod is in the desired radial orientation.

2. The method according to claim 1, wherein rotating the locking holder further includes reaching a rotational limit, releasing the moveable handle, repositioning the locking holder relative to the spinal rod, recompressing the moveable handle and rotating the locking holder to further rotate the spinal rod toward a desired position.

3. The method of claim 2 further comprising repeating the steps of releasing, repositioning, recompressing, and rotating until the spinal rod is in the desired radial orientation.

4. The method according to claim 1, further including attaching a rod reducing device to the head of the bone anchor before releasing the moveable handle.

5. The method according to claim 4, further including utilizing the rod reducing device to push the spinal rod into the head of the bone anchor after the spinal rod is in the desired radial orientation and before releasing the moveable handle.

6. The method according to claim 5, further including locking the spinal rod to the head of the bone screw before releasing the moveable handle.

7. The method according to claim 5, wherein compressing the moveable handle affects engagement of a pawl with an outer surface of the sprocket assembly to radially fix the sprocket assembly relative to the outer body of the locking holder, wherein the sprocket assembly includes radially spaced sprocket sections, each sprocket section forming a portion of the outer surface.

8. The method according to claim 5, wherein releasing the moveable handle moves a pawl out of engagement with an outer surface of the sprocket assembly to permit rotation of the locking holder relative to the sprocket assembly.

9. A method for rotating a spinal rod comprising:
positioning a sprocket assembly of a locking holder over an end of a spinal rod;
compressing a moveable handle of the locking holder towards a fixed handle of the locking holder to move a pawl into engagement with an outer surface of the sprocket assembly such that the sprocket assembly is rotatably fixed relative to the fixed handle and an opening defined by the sprocket assembly is urged inward to reduce a dimension of the opening;
rotating the fixed handle with the moveable handle compressed to affect rotation of the spinal rod about a longitudinal axis defined by the spinal rod;
releasing the moveable handle such that the pawl is permitted to disengage the outer surface of the sprocket assembly; and
rotating the fixed handle with the moveable handle released such that the fixed handle rotates about the sprocket assembly.

10. The method according to claim 9, wherein engagement of the pawl with the outer surface of the sprocket assembly moves a first sprocket section towards a center of the opening defined by the sprocket assembly to reduce the dimension of the opening.

11. The method according to claim 10, wherein engagement of the pawl with the outer surface of the sprocket assembly moves a second sprocket section towards the center of the opening defined by the sprocket assembly to reduce the dimension of the opening.

12. The method according to claim 9, wherein releasing the moveable handle disengages the pawl from the outer surface of the sprocket assembly.

13. The method according to claim 9, wherein compressing the moveable handle towards the fixed handle translates an inner shaft distally within a channel defined by an outer body which forms the fixed handle, the sprocket assembly positioned at a distal end of the outer body, the inner shaft operatively associated with the pawl to move the pawl into engagement with the outer surface of the sprocket assembly.

14. The method according to claim 13, wherein translating the inner shaft distally within the channel includes the inner shaft engaging bearings that cooperate with a bend in the outer body, the bearings engaging a pawl shaft directly coupled to the pawl to move the pawl into engagement with the outer surface of the sprocket assembly.

15. The method according to claim 14, wherein releasing the moveable handle includes translating the inner shaft proximally such that the bearings are permitted to move proximally within the channel.

16. The method according to claim 15, wherein releasing the moveable handle further includes a biasing member engaged with the pawl shaft urging the pawl shaft proximally such that the pawl disengages the outer surface of the sprocket assembly.

17. The method according to claim 16, wherein urging the pawl shaft proximally includes the pawl shaft engaging the bearings to move the bearings proximally within the channel.

* * * * *